US005658258A

United States Patent [19]

Kneer et al.

[11] Patent Number: 5,658,258

[45] Date of Patent: Aug. 19, 1997

[54] ONE PIECE DISPOSABLE APPLICATOR

[75] Inventors: Roland Kneer, Farchant; Christoph Heiland, Saulgrub, both of Germany

[73] Assignee: GAPLAST GmbH, Altenau, Germany

[21] Appl. No.: 528,547

[22] Filed: Sep. 15, 1995

[51] Int. Cl.[6] .................................................. A61M 5/315

[52] U.S. Cl. ........................ 604/220; 604/181; 604/187; 604/218; 604/222

[58] Field of Search .................................. 604/110, 118, 604/158, 218, 220, 223, 233, 227, 228, 181, 187, 184

[56] References Cited

U.S. PATENT DOCUMENTS 5,135,507 8/1992 Haber et al. ............................ 604/187

FOREIGN PATENT DOCUMENTS 9412228 6/1994 WIPO .................................... 604/187

*Primary Examiner*—Corrine M. McDermott
*Assistant Examiner*—Cris L. Rodriguez
*Attorney, Agent, or Firm*—Juettner Pyle Lloyd & Piontek

[57] ABSTRACT

The applicator is assembled from an integral injection-molded part which includes an elongated flat strap from which a piston member projects at a right angle to one side and, at some distance therefrom, a cylinder member including a canula molded thereon projects at a right angle to the other side. The strap forms two spring arms of which the one, being bent by 180°, is first slid over the piston head with a recess. Subsequently, the cylinder is also fit onto the piston head, with the strap section that connects the piston to the cylinder head being also bent by 180°. The piston head snaps in a rear position into the cylinder. The two biased spring arms always bias the piston in the direction of the rear end position, so that the applicator can be operated with one hand to take, for instance, blood from a container. Since the applicator can be manufactured in one piece in an injection-molding process with the aid of a simple on-off tool without slide, it is inexpensive and best suited as a disposable applicator.

21 Claims, 2 Drawing Sheets

ONE PIECE DISPOSABLE APPLICATOR

BACKGROUND OF THE INVENTION

The present invention relates to an applicator, which can, for instance, be used for taking a sample from a blood-containing test tube to test blood. The applicator may also serve as a syringe to administer a drug to a patient, or to take blood directly from a patient. The above are only examples of possible When the piston is retracted in a conventional applicator to suck liquid into the cylinder, the operator normally needs use of both hands, namely one for retracting the piston while the other hand is holding the cylinder. As a consequence, the operator is not capable of performing another operation or, for instance, of holding a receptacle into which the liquid sample is to be discharged from the applicator.

DE 36 09 555 A1 discloses a blood collecting syringe with a canula and a cylinder in which a piston is slidably arranged for drawing a medium into the cylinder. This blood collecting syringe is equipped with racks and gears for operation with one hand only. This is a complicated mechanism for a blood collecting syringe.

EP 166 010 A1 discloses an apparatus for drawing blood from the body, the blood being poisoned by the bite of a reptile. This apparatus comprises a spring between cylinder and piston, the spring being biased such that it acts on the piston with a force driving the same into a retracted position. Moreover, there is a component which serves to sealingly position the apparatus on the skin near the bite wound.

SUMMARY OF THE INVENTION

It is the object of the present invention to provide an applicator such that it can be operated with one hand.

In accordance with the invention, the piston and the cylinder have arranged thereinbetween at least one spring element which pulls or presses the piston back into a retracted position in which the piston only engages into the cylinder with its front end section or piston head. When a blood sample is, for instance, to be taken from a patient or a blood container with the applicator of the invention, the piston is first pressed into the cylinder against the force of a spring, which can easily be done with one hand. The spring element is loaded such that it subsequently moves the piston automatically into a retracted position, with the sample being simultaneously sucked into the cylinder. The applicator is not only suited for receiving and discharging a liquid medium, but aim a gaseous medium.

The spring element may, for instance, be a helical spring which may be arranged between stops or spring seats provided on the cylinder and the piston. The spring element may also be a spring arm consisting of a flexible material, such as a leaf spring or a resilient strap.

In another development of the invention the spring element, preferably in the form of a leaf spring or a flat strap, may be provided on the rear end of the piston which faces away from the cylinder and on the rear end of the cylinder which faces the piston. The spring element may be a component separated from the piston and the cylinder, which is, for instance, snapped into or adhesively bonded to recesses of the piston and the cylinder.

However, the spring element, preferably in the form of a flat strap, is preferably molded integrally onto the cylinder and the piston. This means that it consists of the same material as said components, such as a molded polyolefin.

Furthermore, the spring strap should advantageously extend beyond the cylinder, i.e., a short strap also extends from the diametrically opposite side of the cylinder, the function of such a short strap being explained further below.

In a preferred embodiment of the invention an additional spring arm is biased between piston and cylinder, the additional spring arm being molded onto the piston side which is preferably diametrically opposite to the first-mentioned spring arm, i.e., the two spring arms and the above-mentioned short spring member or strap member are positioned along one axis or in one plane. It should be noted that the invention is not limited to such a form.

At some distance from its free end, the other spring arm comprises a recess which is dimensioned such that the head end of the piston can pass through the recess. Next to the recess there remains a short strap member which projects beyond the piston in the completely assembled state of the applicator, which will be described further below.

As already mentioned, the cylinder, the piston and the strap connecting said components, as well as the further molded straps should preferably be made in one piece, preferably in an injection-molding process. The spring elements or straps extend in a straight line in joint alignment, the piston and the cylinder extending with their axes at a fight angle relative to the longitudinal axis of the straps, i.e., in opposite directions.

The applicator is mounted such that the spring arm comprising the recess is first bent by 180° and guided with the recess over the head end of the piston. The other spring arm is then also bent by 180°, the cylinder being fitted onto the piston so that the piston head engages into the cylinder. The two projecting short spring members come into contact with the associated spring arms, thereby supporting the latter.

When the spring arms are bent, they are being loaded so that they tend to retract the piston from the cylinder.

When the spring arms and the short spring or strap members are not integrally formed with the cylinder and the piston, they may consist of a single separate component which, as mentioned above, may, for instance, be snapped into recesses of the rear sections of the piston and the cylinder or may, for instance, be adhesively bonded there.

To prevent the piston from being pulled out of the cylinder by a spring force, a ring bead or a so-called olive may be molded onto the outside of the head end of the piston. A suitable blocking means, such as a ring bead or an inwardly projecting hook, may be provided on the inner wall of the cylinder, the free inner diameter being slightly smaller than the outer diameter of the piston head in the area of the ring bead or the olive. When the piston head is forced through the blocking means by applying a certain force, this will create a defined end position for the piston that can no longer be exceeded by the piston automatically.

In accordance with another inventive suggestion, a further blocking means whose diameter is also slightly smaller than the maximum outer diameter of the piston head may be positioned on the inner wall of the cylinder next to the above-described end position of the piston head. Furthermore, the interior of the cylinder next to this second blocking means should, in an especially advantageous manner, be smaller than the outer diameter of the piston in the area of the olive, ting bead or the like, so that the piston in the entire area following the second blocking means is sealed relative to the inner cylinder wall. In the area of the second blocking means the free diameter of the cylinder is reduced not only in comparison with the area of the rear end position, but also in comparison with the front cylinder portion. Such a configuration offers considerable advantages.

In conventional syringes the piston will remain in the advanced position in which it is pushed into the cylinder more or less entirely, as long as the syringe is not put into use. Such a position shall here be designated as "storing position". Since the piston is radially oversized because of the necessary seal relative to the inner cylinder wall, this has the effect that the cylinder in this storing position is expanded, i.e., it is given an annular bulge. When the syringe is put into use, the piston is retracted to suck liquid and is subsequently pushed forward again for administering a drug to a patient. This will be done against the action of a constant counterforce until the piston reaches the area of the front bulged storing position in which the counterforce is abruptly reduced. As a consequence, the piston is bound to be advanced in this area more rapidly, so that a considerably increased amount of liquid is suddenly pressed out. This has, among other things, the disadvantage that great pain might be caused thereby.

In the applicator of the invention, the storing position is located in the rear area of the cylinder between the two blocking means, for instance between two spaced-apart ring beads. In this storing position the free inner diameter of the cylinder may be just as great as the maximum outer diameter of the cylinder head, since there need not be any sealing. When the applicator is put into use, the piston is pushed into the front end position, returning automatically—due to spring force—to the blocking means positioned in front of the storing piston, for instance, to the ring bead provided there, with the piston head being sealed in said area due to a slight oversize. The ring bead which limits the automatic return thereof prevents the piston from reaching the storing position again, thereby defining the so-called dosage end position from which the piston advances to discharge the liquid received. The liquid is thus discharged via the whole piston stroke against a constant resisting force, so that the liquid can be discharged at a rate and an mount which remains constant.

In accordance with another suggestion of the invention, the piston head may be stopped in the advanced position in the cylinder. This is especially expedient for applications in the case of which an injection is first given to a patient and blood is subsequently to be taken after a short time interval has passed. In the applicator of the invention, a locking mechanism may, for instance, be provided in the advanced end position for retaining the piston until the lock is released, so that the applicator then takes blood automatically by spring force. To retain the piston in the advanced position the inner wall of the cylinder may, for instance, have formed thereon a ring bead which will retain the piston until a sufficiently great force acts on the piston by laterally compressing the spring straps, so that the piston is retracted via the ring bead.

The tip of the cylinder may consist of a plastic material in some cases of application, and it should preferably integrally be molded onto the cylinder. A Luer cone according to DIN 13050 into which a metal canula according to DIN 13097 can for instance be inserted may also be molded onto the cylinder. The design can here be chosen such that a metal canula is pressed or adhesively bonded in place in the front end section of the cylinder or is injection-molded therearound.

The applicator of the invention can advantageously be produced in an injection-molding process without the invention being limited thereto. In case of a production by way of an injection-molding process a simple on-off tool without slide may be used, whereby the applicator can be produced in an especially inexpensive manner. It is thus also especially suited for use as a disposable applicator.

The magnitude of the spring force can, for instance, be set to the desired degree by selecting a suitable wall thickness for the spring straps.

BRIEF DESCRIPTION OF THE DRAWINGS

Preferred embodiments of the invention shall now be explained in more detail with reference to the drawing, in which.

DESCRIPTION OF THE PREFERRED EMBODIMENTS

The figures illustrate-embodiments of an applicator which is especially suited for taking blood samples from blood-containing receptacles. Other uses might require a larger size applicator.

Figure 1:
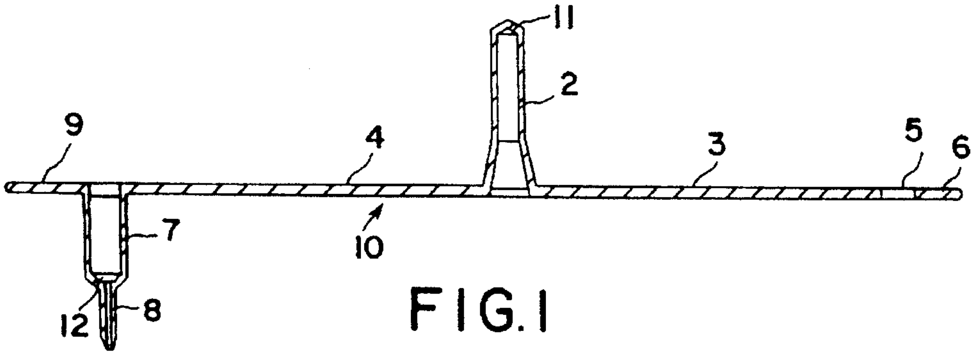
FIG. 1 is a front view of a first embodiment of an injection-molded part for an applicator of the invention on an enlarged scale.

FIG. 1 shows an integral injection-molded part 1 approximately on a scale of 2:1. The injection-molded part comprises an elongate tubular member having a closed end which serves as a piston 2 and has molded thereon at both sides flat straps that serve as spring arms 3 and 4. Spring arm 3 includes a recess 5 which is dimensioned such that piston 2 can extend therethrough. The spring arm is continued behind recess 5 in an extension member 6.

Spring arm 4 leads to a member which serves as a cylinder 7 and has molded thereon a canula or tip 8. Spring arm 4 is continued at the other side of cylinder 7 in an extension member 9. Spring arms 3, 4 and extension members 6, 9 form part of a straight flat strap 10 from which piston 2 and cylinder 7 extend away at a right angle.

The closed head 11 of piston 2 has a flat conical shape which corresponds to the front end section 12 of the inner cylinder chamber. Liquid inside cylinder 7 can thereby be pressed out entirely.

Figure 2A:
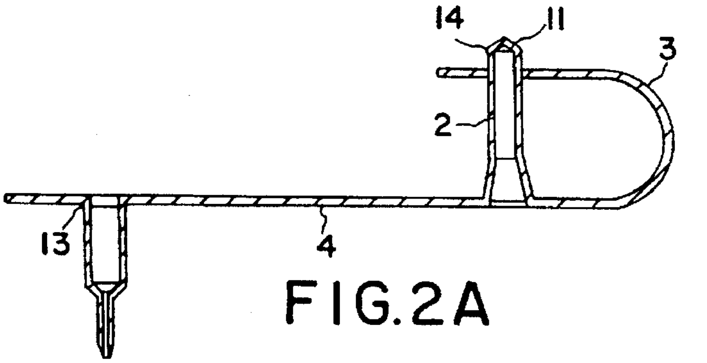
FIGS. 2A and 2B illustrate the two assembling steps for completing the applicator.
Figure 2C:
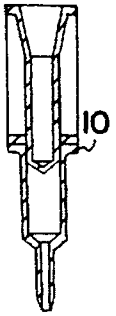
FIG. 2C is a side view of the finished applicator.
Figure 2B:
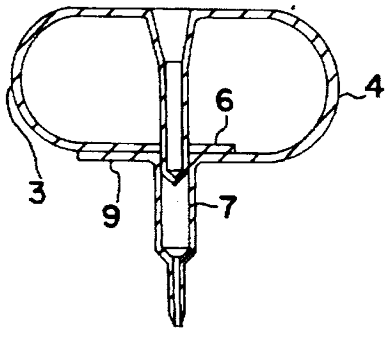

The assembly of the applicator is shown in FIGS. 2A and 2B. First of all, spring arm 3 is slid over piston 2, with piston head 11 passing through recess 5. In a second assembling step, piston head 11 is then inserted into cylinder 7, with spring arm 4 being also bent by 180°.

A ring bead which projects slightly inwardly radially is provided on the upper edge of the inner wall of cylinder 7, and a ring bead 14 which slightly projects beyond the adjacent piston wall is also formed on piston head 11 on the outside. The dimensions are chosen such that the piston head can only pass with its ring bead 14 through ring bead 13 by applying a certain force, with ring bead 13 acting as a blocking means to prevent piston head 11 from exiling from cylinder 7 due to the force of spring arms 3, 4. In the area of ring bead 14 piston 2 is slightly oversized in comparison with the clear interior of cylinder 7, whereby a liquid-tight seal is created between piston and cylinder.

FIG. 2C is a side view of the applicator. The figure shows that strap 10 has a width which is slightly greater than the outer diameter of the piston and the cylinder.

FIG. 2B shows that the extension members 6 and 9 come to rest on spring arms 4 and 3, whereby the spring arms take on the illustrated symmetrical form.

Figure 3:
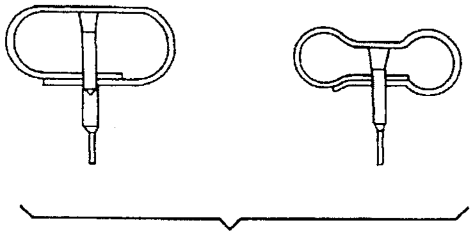
FIG. 3 shows views of the ready applicator in the inoperative state and the operative state.

On a scale of 1:1, FIG. 3 shows the applicator of FIGS. 1 to 2 at the right side in the operated state and at the left side in the state in which the piston is in the retracted initial position.

Figure 4:
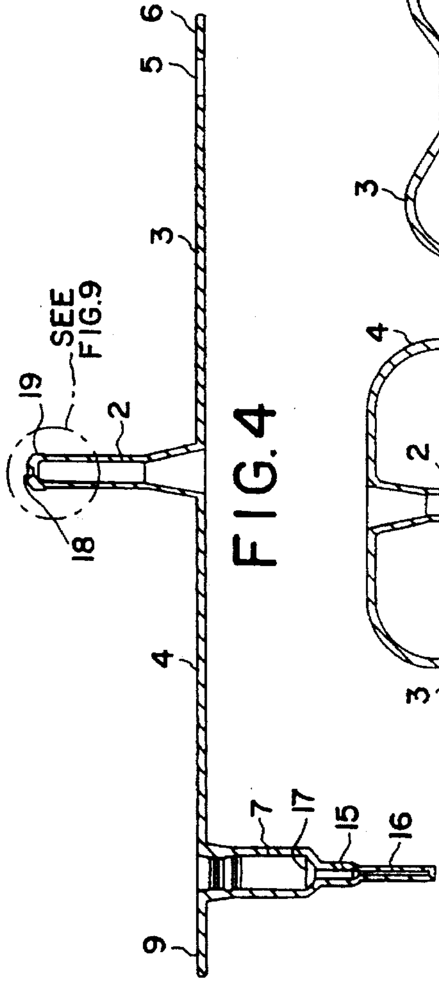
FIG. 4 shows a further embodiment of an injection-molded part for an applicator.

FIG. 4 shows a second embodiment of an applicator. The components which correspond to those of the first embodiment are designated by identical reference numerals and are here not mentioned again.

Figure 6:
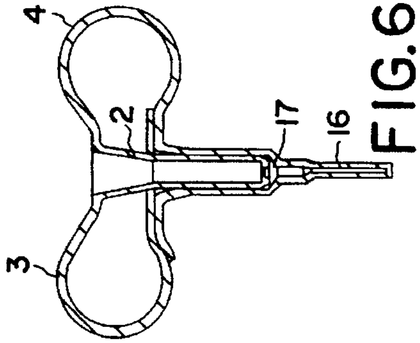
FIG. 6 shows the applicator according to FIG. 5, with the piston being pushed forward.

Cylinder 7 of the second embodiment has molded thereon an attachment 15 which has inserted thereinto a stainless-steel canula 16 which projects for a short way into the interior of cylinder 7. The front end of piston head 19 includes a recess 18 which is entered by the projecting end 17 of needle 16 in the advanced position of piston 2, as can also be seen in FIG. 6.

Figure 5:
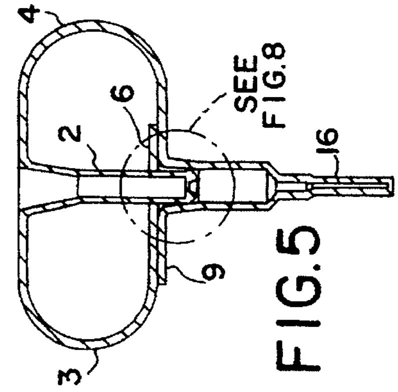
FIG. 5 shows the second embodiment of the applicator assembled to be ready for use.
Figure 8:
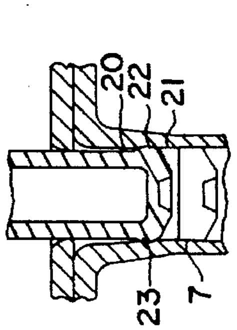
FIG. 8 is another enlarged illustration of the area of the storing position and the dosage end position.

FIG. 8 is an enlarged view of the area of the rear end section of piston 2 as marked by a broken circle in FIG. 5. The inner wall of cylinder 7 has formed thereon two axially spaced-apart ring beads 20 and 21 which have positioned thereinbetween an annular trough-like recess 22 which is engaged by an outer ring bead or olive 23 on piston head 19 in the so-called storing position. The outer diameter of the piston head in the area of olive 23 corresponds substantially to the inner diameter of cylinder 7 in the area of the annular recess 22, so that the cylinder wall is not expanded.

Following the front ring bead 21, cylinder 7 has a constant diameter which is slightly smaller than the outer diameter of piston head 19 in the area of olive 23, so that upon operation of the applicator a liquid-ensured between olive 23 and the inner cylinder wall.

Figure 7:
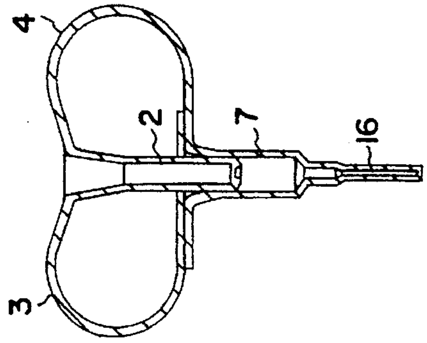
FIG. 7 shows the applicator according to FIG. 5 with the piston being in the dosage end position.

In the ready assembled state of the applicator, which is shown in FIG. 5, piston 2 is pressed with its ring bead 23 by the application of a certain force through the rear ring bead 20 of the cylinder, the piston being blocked in said position in both axial directions by the ring beads 20 and 21. When the applicator is operated to take, for example, blood from a container, piston 2 is forced through the front ring bead 21 and advanced into the position shown in FIG. 6, from which piston 2 will automatically return due to the force of spring arms 3 and 4 into the dosage end position in which olive 23 of the piston head is positioned below the ring bead 21 next thereto in the illustration of FIG. 8. The dosage end position is illustrated in FIG. 7.

Figure 9:
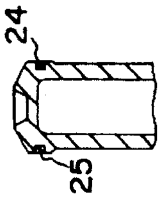
FIG. 9 shows an alternative embodiment of the piston head.

FIG. 9 shows an alternative embodiment of the piston head which is here provided with an annular groove 24 into which an O-ring 25 is inserted.

Figure 10:
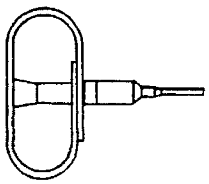
FIG. 10 illustrates the second embodiment of the applicator on a natural scale.

FIG. 10 shows an applicator on a scale of 1:1 for taking a blood sample.

What is claimed is:

1. An applicator for withdrawal and dispensing of fluids comprising a cylinder having a first and a second end, a canula at said first end of said cylinder, a piston slidably mounted in the cylinder toward and away from said canula, a first spring arm means of flexible material connected between said cylinder and said piston for biasing said piston away from said canula externally of said cylinder, and a second spring arm means of flexible material extending from said piston for biasing said piston away from said canula externally of said cylinder.

2. The applicator according to claim 1, wherein said first spring arm means is mounted on said piston and the second end of said cylinder.

3. The applicator according to claim 2, wherein said first spring arm means is integrally molded on said cylinder and said piston.

4. The applicator according to claim 3 wherein said first spring arm means comprises an extension member extending beyond said cylinder.

5. The application according to claim 1 wherein said second spring arm means is molded onto the piston and is diametrically opposite to said first spring arm means.

6. The applicator according to claim 5, wherein said second spring arm means has a free end and a recess in said free end which is dimensioned to receive said piston.

7. The applicator according to claim 6, wherein said second spring arm means comprises an end section extending beyond said recess.

8. The applicator according to claim 1, wherein a ring bead is molded onto the outside of said piston.

9. The applicator according to claim 1, wherein an annular groove, is formed in the head end of said piston.

10. The applicator according to claim 1, wherein said cylinder comprises an inner wall, and wherein a first blocking means is molded onto the inner wall of said cylinder for holding said piston in a defined initial position.

11. The applicator according to claim 10, wherein said first blocking means is a ring bead.

12. The applicator according to claim 10, wherein said first blocking means has inwardly projecting hook-like attachments.

13. The applicator according to claim 10, additionally comprising second blocking means within said cylinder spaced from said first blocking means.

14. The applicator according to claim 1, wherein said canula comprises a molded plastic tip.

15. The applicator according to claim 1, wherein a hollow cone is molded onto said cylinder for holding a metal canula.

16. The applicator according to claim 15, wherein a metal canula is secured to said hollow cone.

17. The applicator according to claim 1, wherein said cylinder, piston and spring means are produced by an injection-molding process.

18. The applicator according to claim 17, characterized in that said cylinder, piston and spring means are integrally produced.

19. The applicator according to claim 1, wherein the applicator is composed of a thermoplastic polymer.

20. The applicator according to claim 1, wherein said first and second spring means comprise a leaf spring in the form of a continuous compressible loop between the piston and cylinder.

21. A syringe comprising a piston in the form of an elongate tube having a dosed end and an outer end, a cylinder having first and second ends, a canula mounted on said first end, said second end being open and slidably receiving the closed end of said tube, and a leaf spring in the form of a loop between said cylinder and the outer end of said tube, said leaf spring biasing the closed end of said tube away from the first end of said cylinder.

* * * * *